(12) United States Patent
Slaon, III et al.

(10) Patent No.: US 6,415,455 B1
(45) Date of Patent: *Jul. 9, 2002

(54) STOOL SPECIMEN COLLECTOR

(75) Inventors: Walker M. Slaon, III, Berlin, MA (US); Stanley N. Lapidus, Bedford, NH (US)

(73) Assignee: Exact Sciences Corporation, Maynard, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/022,648

(22) Filed: Dec. 17, 2001

Related U.S. Application Data (63) Continuation of application No. 09/804,861, filed on Mar. 13, 2001, now Pat. No. 6,351,857, which is a continuation of application No. 09/303,988, filed on May 3, 1999, now abandoned.

(51) Int. Cl.[7] .............................................. A47K 11/00
(52) U.S. Cl. ..................... 4/315; 4/479; 4/484; 383/33; 383/72; 604/317
(58) Field of Search ........................... 4/315, 449, 452, 4/479, 480, 483, 484; 383/33, 34, 63–65, 97, 72, 43; 604/317, 322

(56) References Cited

U.S. PATENT DOCUMENTS

| | | |
|---|---|---|
| 348,738 A | 9/1886 | Hackenberg .................... 4/484 |
| 408,607 A | 8/1889 | Flint |
| 2,506,502 A | 5/1950 | Herrmann ....................... 4/142 |
| 2,514,750 A | 7/1950 | Dobbs et al. ................... 150/3 |
| 2,537,504 A | 1/1951 | Anderson ....................... 4/237 |
| 2,801,426 A | 8/1957 | Gorce et al. .................... 4/142 |
| 3,416,164 A | 12/1968 | Ekrut ............................. 4/142 |
| 3,737,920 A | 6/1973 | Savee ............................. 4/142 |
| 3,775,777 A | 12/1973 | Roberts, Jr. ........................ 4/1 |
| 4,067,443 A | 1/1978 | Greenwald .................. 206/459 |
| 4,101,279 A | 7/1978 | Aslam .......................... 23/259 |
| 4,309,782 A | 1/1982 | Paulin ............................ 4/661 |
| 4,343,053 A | 8/1982 | O'Connor ...................... 4/452 |
| 4,367,750 A | 1/1983 | Levine ......................... 128/638 |
| 4,445,235 A | 5/1984 | Slover et al. ................. 4/144.2 |
| 4,492,124 A | 1/1985 | Fleisher et al. .......... 73/864.44 |
| 4,519,095 A | 5/1985 | Clayton ........................ 383/86 |
| 4,678,559 A | 7/1987 | Szabados ..................... 209/17 |
| 4,735,905 A | 4/1988 | Parker ......................... 436/174 |
| 4,759,086 A | 7/1988 | Booth-Cox .................... 4/451 |
| 4,872,420 A | 10/1989 | Shepard .......................... 119/1 |
| 4,872,868 A | 10/1989 | Chevallier .................. 604/327 |
| 4,982,615 A | 1/1991 | Sultan et al. .................. 73/864 |
| 5,083,349 A | 1/1992 | Axtell .......................... 24/429 |
| 5,149,506 A | 9/1992 | Skiba et al. ................. 422/102 |
| 5,463,782 A | 11/1995 | Carlson et al. ................. 4/661 |
| 5,832,145 A | 11/1998 | Dais et al. ................... 383/211 |

FOREIGN PATENT DOCUMENTS

| | | | |
|---|---|---|---|
| EP | 0 022 377 A1 | 1/1981 | .......... G01N/33/52 |
| EP | 0 187 684 A2 | 7/1986 | .......... A61B/10/00 |
| FR | 2 720 919 A1 | 6/1994 | .......... A47K/11/06 |
| FR | 2 740 672 A1 | 11/1995 | .......... A47K/17/00 |
| GB | 2 196 246 A | 4/1988 | .......... A47K/11/06 |
| GB | 2 229 699 A | 10/1990 | .......... A47K/11/06 |

*Primary Examiner*—Charles R. Eloshway
(74) *Attorney, Agent, or Firm*—Testa, Hurwitz & Thibeault LLP (57) ABSTRACT

The invention provides an apparatus for obtaining a stool specimen. The apparatus comprises a housing, a collection bag, a slider to close the collection bag and a draw string to move the slider. A user places the apparatus on a toilet, deposits a first stool into the collection bag, then pulls the draw string to move the slider to close the collection bag thereby allowing the user to urinate or further defecate.

8 Claims, 7 Drawing Sheets

STOOL SPECIMEN COLLECTOR

RELATED APPLICATIONS

This application is a continuation application of U.S. application Ser. No. 09/804,861, filed on Mar. 13, 2001, now U.S. Pat. No. 6,351,857, which is a continuation in part of U.S. application Ser. No. 09/303,988, filed on May 3, 1999 now abandoned.

TECHNICAL FIELD

This invention relates generally to an apparatus for collecting biological specimens. More particularly, the invention relates to an apparatus for the collection and transportation of stool specimens.

BACKGROUND OF THE INVENTION

Stool specimens are used with increasing frequency for the screening and diagnosis of disease. Evidence of parasitic, infectious, or inherited disease may be found in stool. For example, the presence of carcinoembryonic antigen or blood in stool is indicative of colorectal cancer. Stool-based assays for parasitic organisms are also widely available.

A significant problem with using stool specimens in screening or diagnosis arises in the collection of the specimen. Depending on its physical state, the specimen may be difficult to collect into a container. Moreover, the handling of a specimen raises sanitary concerns. Merely obtaining a specimen may increase the risk of disease transmission, especially if sanitary procedures are not followed. This is especially true if the patient is responsible for obtaining the specimen. The odor often associated with a stool specimen, and the frequent need to transport the specimen also contribute to the problems associated with sample collection.

Attempts have been made to solve these problems. For example, Aslam, U.S. Pat. No. 4,101,279, reports a disposable bowl adapted to fit onto a toilet for collection of stool. Such a device eliminates the need for the patient to handle the specimen directly. However, the patient (or technician) is still exposed to the sample, resulting in possible contamination and the presence of odor. Moreover, the Aslam device contains blades for homogenization that may present a danger to the patient.

Paulin, U.S. Pat. No. 4,309,782, also reports a bag adapted to fit onto a toilet for collection of stool. The device reported by Paulin also provides for scraping excess stool out of the bag after use.

While these and other devices of the art have attempted to solve the problems associated with collection of stool, none have provided a solution that minimizes handling of the specimen, minimizes odor and contamination, and provides for easy transport of the specimen. Accordingly, there remains a need in the art for a device for safe and secure collection of stool.

SUMMARY OF THE INVENTION

The present invention provides an apparatus for a collecting, storing, and/or shipping a stool specimen. Generally, the invention provides a housing having attached thereto a retractable bag for collecting the specimen. The bag is retracted by a draw string or cord (e.g., a lanyard) attached thereto, or preferably by a slider attached to the housing and to which the draw string is attached for moving the slider. In use, the patient places a device of the invention on a toilet, deposits stool into the bag, and pulls the draw string thereby to engage the slider to retract the bag. The patient may then urinate or further defecate. In a preferred embodiment, the bag is retracted into a portion of the housing. An advantage of a device of the invention is that the bag can be closed by the patient while the patient is still seated on the device.

Also in a preferred embodiment, the housing is shaped to fit onto a toilet seat. A preferred housing releasably attaches to the toilet seat or may comprise a non-slip surface for contacting the toilet. The housing may comprise padding to increase patient comfort. A preferred housing is preferably constructed of cardboard or plastic but may be constructed of any useful material. The housing may comprise supports for resting the apparatus on a toilet seat. The supports may be folded over the housing for compact transportation of the apparatus.

A stool specimen collector of the invention comprises a bag for collection, storage, and/or transport of the specimen. Preferably, a bag for use in an apparatus of the invention is releasably attached to the housing, preferably on the underside of the housing. In a preferred embodiment, the bag may be movably attached in a groove in the housing in order to facilitate closure of the bag. However, the bag may be fixedly attached to the housing at the convenience of the manufacturer or the technician. The bag is constructed of any suitable material such as polyethylene or PVC, and is preferably opaque. In a preferred embodiment, the bag may contain a buffer, or other additives to retard degradation of the specimen, and to optionally reduce odor.

A preferred apparatus comprises a slider attached to a draw string for closing the bag. In a preferred embodiment, the bag comprises a spring beam holding the bag in an open position. The spring beam deforms to a closed position under the housing when the bag is closed. The slider is preferably engaged on the underside of the housing, such that when the draw string is pulled the slider sweeps the underside of the housing, thereby gathering the perimeter of the bag and causing the bag to close. In an alternative embodiment, the draw string itself is attached to the bag for closure and no separate slider is used. Thus, the draw string may be any material or configuration that is capable of closing the bag. It is not necessary for the draw string to remain attached to the bag after closure. Thus, the draw string may be detachable. A preferred draw string is constructed of nylon, and may be a loop, straight chord, braided, or any other configuration capable of closing the bag. Preferred bag closure mechanisms include a flexible tongue and groove assembly, a zipper, a thermal seal, an adhesive, a "zip-lock" assembly and others known in the art to effect closure of the open perimeter of a collection bag.

Also in a preferred embodiment, instructions for using the apparatus are attached to or printed on the housing.

Another embodiment of the invention provides methods for obtaining a stool specimen. In one embodiment, methods comprise placing a stool collector apparatus over a toilet, sitting over or on the apparatus, evacuating a stool into the collection bag, pulling the draw string to close the collection bag, and retracting the collection bag under the housing or bracket. A particular advantage of this embodiment is the collection bag is closed while the patient is still seated.

Additional aspects and advantages of the invention are apparent upon consideration of the following detailed description thereof.

BRIEF DESCRIPTION OF THE DRAWINGS

In the drawings, like reference characters generally refer to the same part throughout the different views. Also, the drawings are not necessarily to scale, emphasis instead being place upon illustrating the principles of the invention.

FIG. 3 is a schematic diagram illustrating the method of using the stool specimen collection apparatus.

DETAILED DESCRIPTION OF THE INVENTION

Figure 1A:
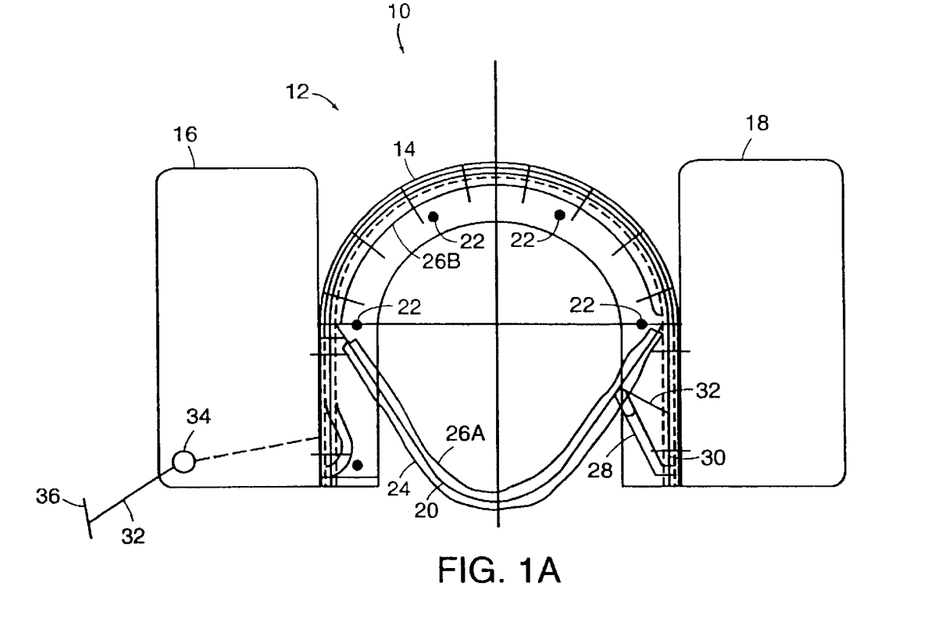
FIG. 1A is a bottom view of the stool specimen collector apparatus.
Figure 1B:
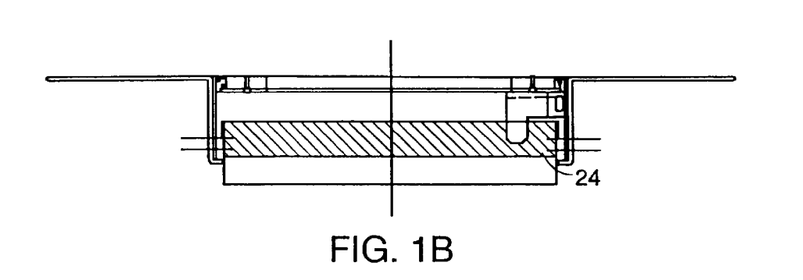
FIG. 1B is a front view of the stool specimen collector apparatus.

Referring to FIGS. 1A and 1B, shown is a bottom view (1A) and a side view (1B) of a preferred stool specimen collector apparatus 10. The stool specimen collector apparatus 10 comprises a housing 12 which comprises a center U-shaped support 14 which is connected to two side supports 16 and 18. The side supports 16 and 18 are hinged to center support 14 in such a way as to support the stool specimen collector apparatus 10 when it is placed on a toilet (not shown), and to allow the side supports 16 and 18 to be folded under the center support 14 when the stool specimen collector apparatus 10 is not being used.

Figure 2A:
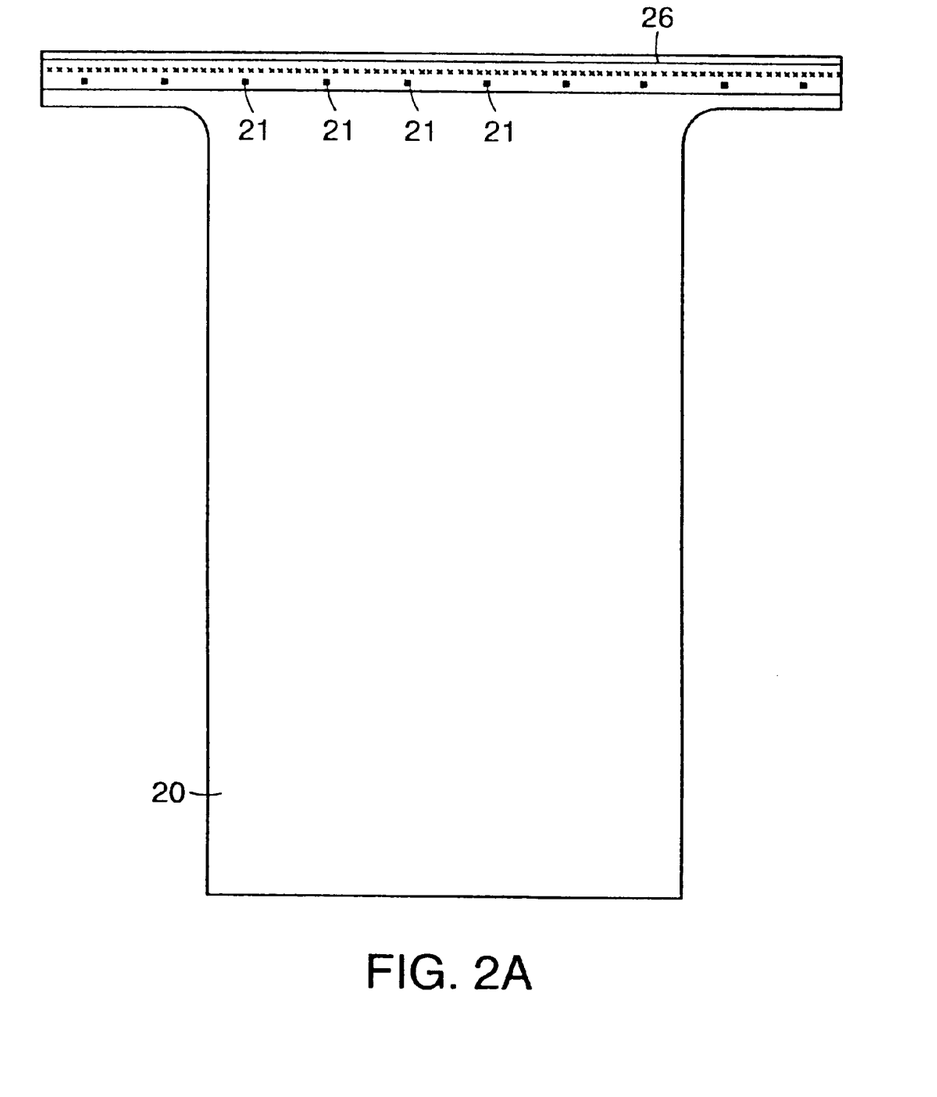
FIG. 2A is a side view of the collection bag.
Figure 2B:
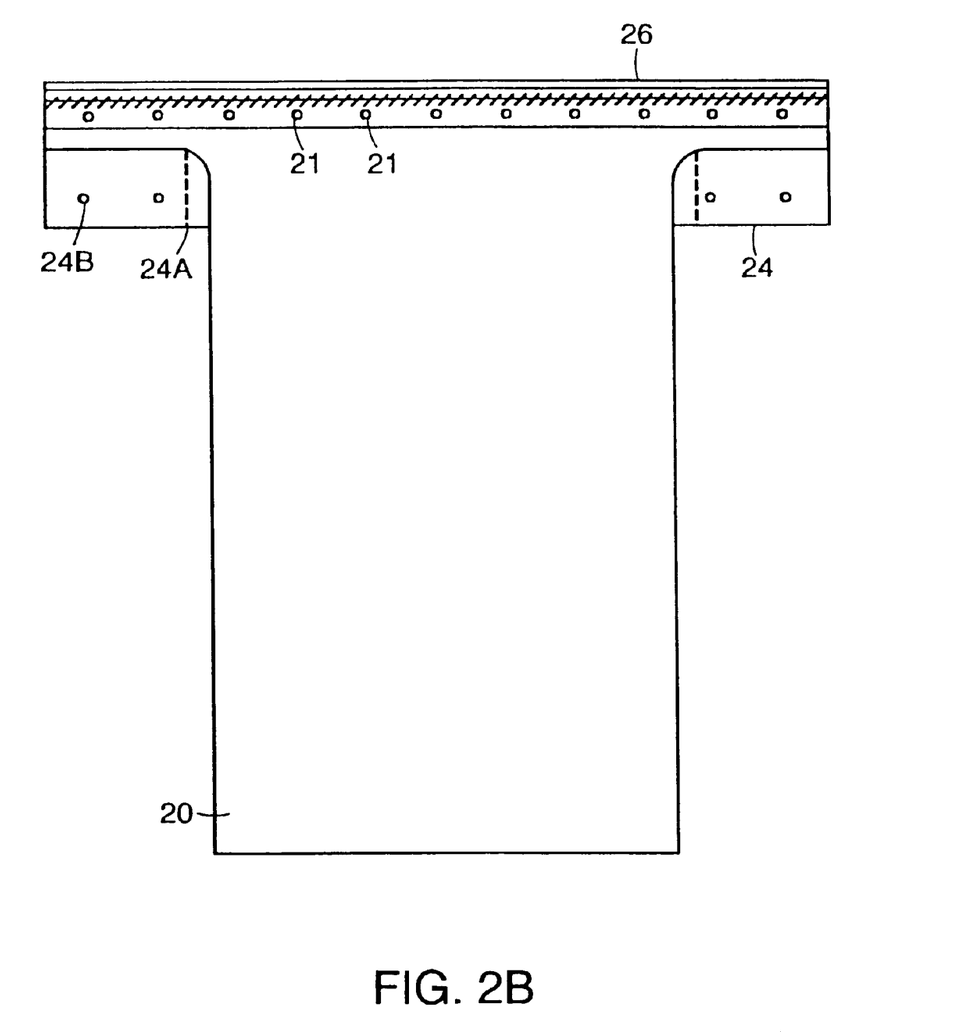
FIG. 2B is a side view of the integral assembly of the collection bag, zipper and spring beam.

At least a portion of a collection bag 20 is attached to the center support 14. Preferably, the collection bag 20 is removably attached to the center support 14. In FIG. 1A and FIG. 4E, the rear portion of the collection bag 20 is attached by rivets 22 through holes 21 in a zipper flange 26C of a zipper 26 which is attached to the collection bag 20. The rivets 22 then pass into holes 14C located in the center support 14. Alternatively, attachment of the collection bag 20 is accomplished by other known methods, such as heat staking. FIG. 2A is a side view of the collection bag 20, and FIG. 2B is a side view of the integral assembly of the collection bag, zipper 26 and spring beam 24.

As shown in FIGS. 1A and 1B, the front of the collection bag 20 also includes a spring beam 24 which is preferably an integral part of the collection bag 20. The spring beam 24 is a narrow strip of resiliently biased material but has sufficient vertical height to prevent vertical deflection of the collection bag 20 away from the center support 14. The spring beam 24 is initially flexed outward toward the front of the toilet bowl when the apparatus is in use, and provides support for the collection bag 20 in the open position.

A preferred collection bag 20 comprises a thin flexible plastic film or any other material known to those skilled in the art for containing a biological sample. The collection bag 20 may be opaque to prevent the individual from viewing the contents, or the collection bag 20 may be clear to allow visual analysis by technicians.

As shown in FIG. 1A, FIG. 2A, FIG. 2B, and FIG. 4E, the top edges of the collection bag 20 preferably have a zipper 26, in which the front portion of the collection bag 20 contains a first portion of the zipper 26A, and the back portion of the collection bag 20, which is attached to center support 14, contains a second portion of the zipper 26B. In one embodiment of the first portion of the zipper 26A is the male portion of the zipper 26 and the second portion of the zipper 26B is the female portion of the zipper 26. In another embodiment the zipper 26 runs the entire length of the open perimeter of the collection bag 20. A preferred zipper is an ITW Maxgrip UX202T. The collection bag 20 may have alternative closures, such as an adhesive closure, or others known in the art.

Mounted to the underside of the center support 14 is a slider 28 that runs along slider track 30. The slider 28 is attached to the zipper 26 of collection bag 20. The slider 28 is attached to a draw string 32. The draw string 32 extends from the slider 28, around the center support 14, under side support 16, and extends through an opening 34 in side support 16. A handle 36 is attached to the end of the draw string 32 as shown in FIG. 1A.

Figure 4A:
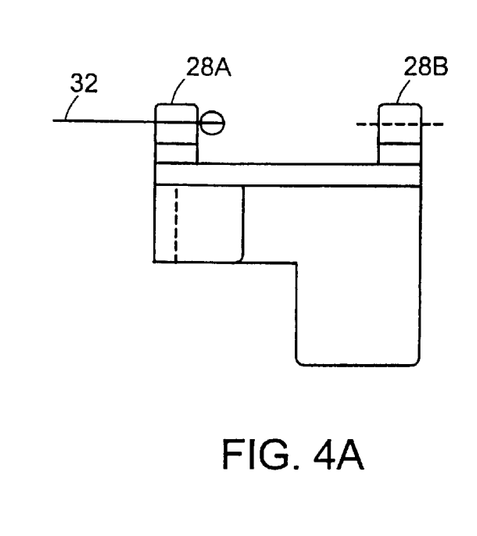
FIG. 4A is a side view of the slider.
Figure 4B:
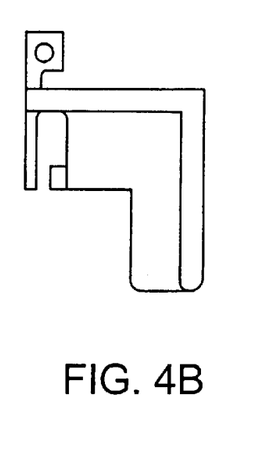
FIG. 4B is a front view of the slider.
Figure 4C:
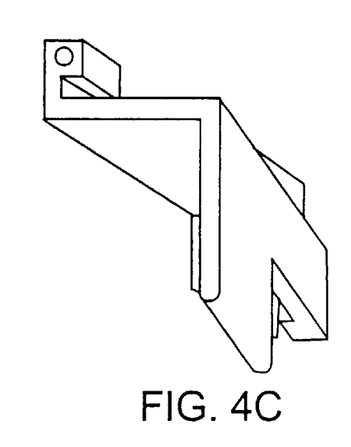
FIG. 4C is a perspective view of the slider.
Figure 4D:
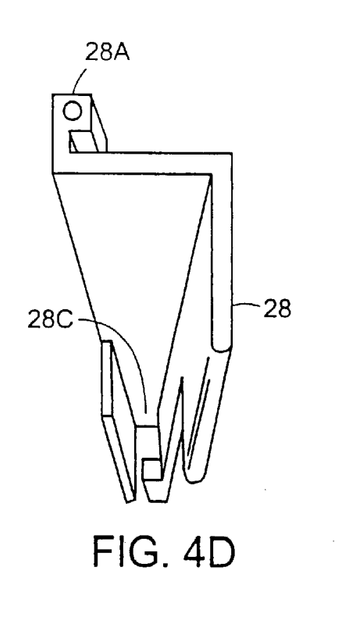
FIG. 4D is a perspective view of the slider showing the slider closure area.
Figure 4E:
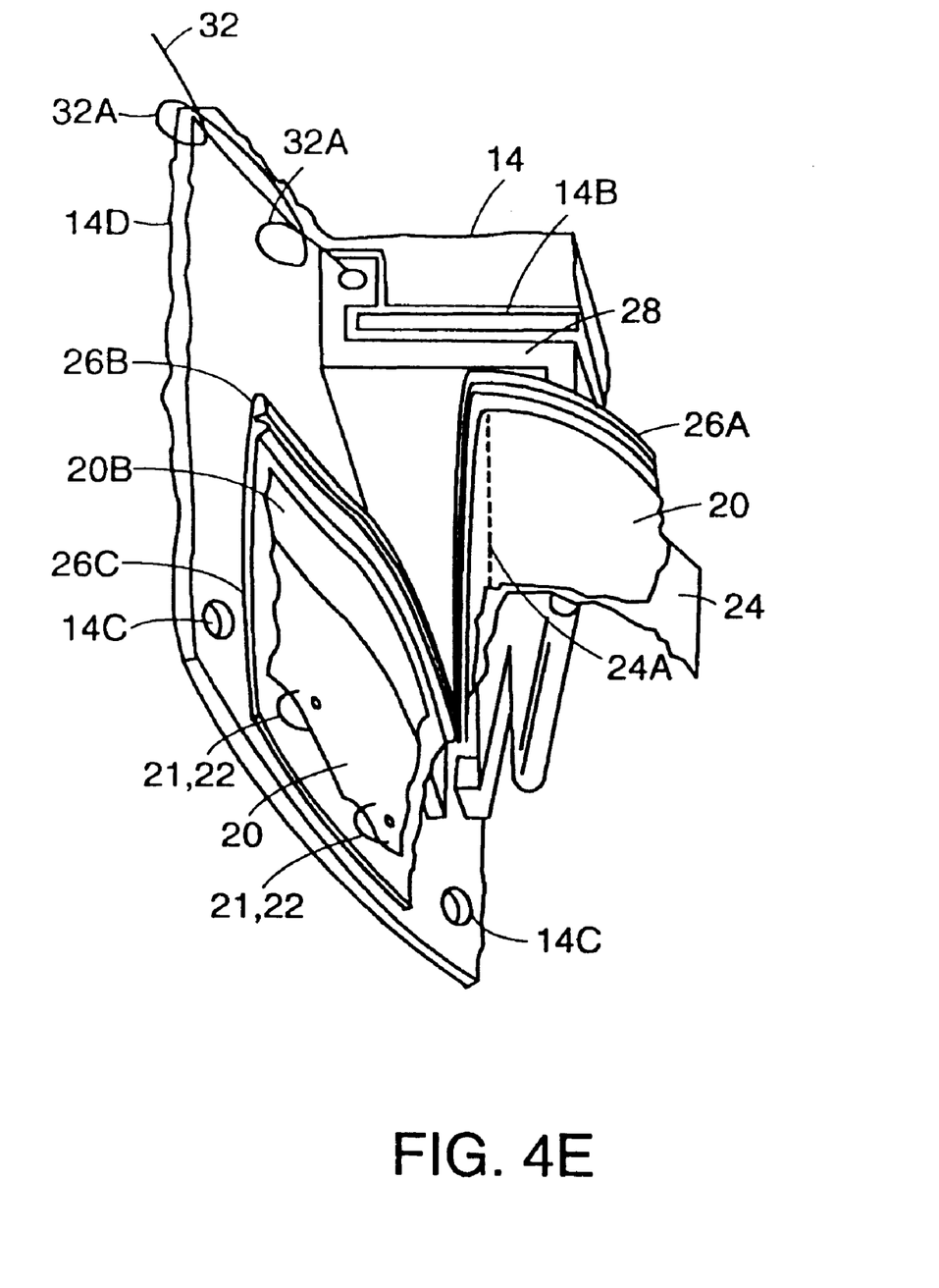
FIG. 4E is a perspective view of the slider, zipper, collection bag and draw string.

In further detail, the slider 28 has two blocks 28A and 28B on its top edge as shown in FIG. 4A which also shows the draw string 32 is attached to block 28A. As shown in FIG. 4E, the draw string 32 is a heavy nylon monofilament which is molded by using heat into a high pitch helix 32A, where the diameter of the helix 32A is equal to the width of the slider track 30, and is sufficiently large to prevent the draw string 32 from falling out of the slider track 30 through the gap between the center support 14 and a slider track plate 14B. Blocks 28A and 28B run in the slider track 30. A beginning portion of the zipper 26 is zipped together while the collection bag 20 is open by sliding the slider 28 over the begirining portion of zipper 26. As a user pulls handle 36 and draw string 32, the slider 28 moves along the slider track 30 which results in the female portion of the zipper 26B and the male portion of the zipper 26A being brought together and engaged in the closure area 28C of the slider 28.

The collection bag 20 is bonded together to both flanges of the zipper 26. The collection bag bond area 20B is above the holes 21 in the zipper flange 26C on the female portion 26B of the zipper 26, allowing rivets 22 to enter those holes 21 in the zipper flange 26C in the space between the body of the collection bag 20 and the zipper flange 26C, and then into the holes 14C in the center. support 14. This arrangement permits the bag assembly of the bag 20, the zipper 26 and the spring beam 24 to be removably affixed to the center support 14 without penetrating the wall of the collection bag 20. FIG. 2B shows the spring beam 24 is creased near both ends of the beam at 24A to permit the spring beam 24 to assume either the open state shown in FIG. 1A, or the closed U shape when the collection bag 20 is closed. A front edge of the slider 28D (FIG. 5) deflects the spring beam 24, first into an S shape while the zipper 26 is being closed. Then when the slider 28 has reached the far end of the slider track 30, the spring beam 24 has become a U shape in close proximity to the flange 14D of the center support 14. The collection bag 20 in the closed position is stored under the center support 14.

Figure 5:
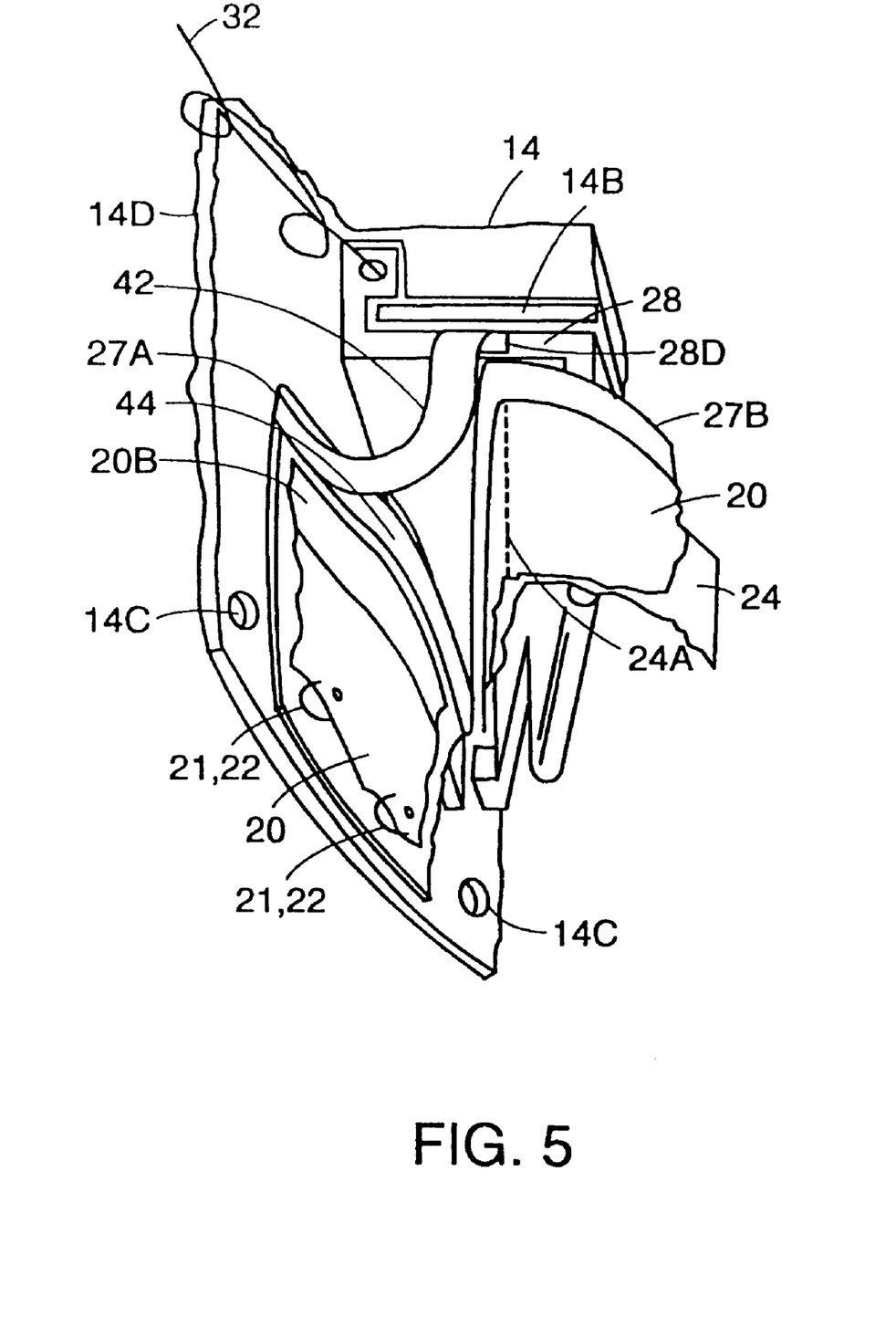
FIG. 5 is a perspective view of the slider, adhesive, collection bag and draw string.

FIG. 5 illustrates an embodiment of the invention that uses an adhesive seal instead of a zipper to seal the collection bag 20 closed. FIG. 5 illustrates how a release paper strip 42 passes from the center support 14 (not shown), through a slider slot 28D, and onto an adhesive area 27A on a top side of the collection bag 20. An end of the release paper strip is attached to the center support 14 above the starting position of the slider 28 when the collection bag 20 is in the open position. In one embodiment, the end of the release paper strip can be attached to the center support 14 by using a small clamp plate held down by a screw. In another embodiment, the end of the release paper strip can be captured between the center support 14 and the slider track plate 14B. The release paper strip 42 on the adhesive area 27A covers an adhesive 44. As the slider 28 moves along the slider track 30, the release paper strip 42 is lifted off the adhesive 44. The slider closure area 28C then pushes the adhesive area 27A, with the exposed adhesive 44, together with an opposite top side of the collection bag 27B, to seal the collection bag 20 together forming an adhesive seal in a manner similar to the closure of zipper 26.

A method for using a stool specimen collector apparatus 10 is illustrated in FIG. 3. An individual places the stool specimen collector apparatus 10 on a toilet 8. The user then sits on or over the stool specimen collector apparatus 10 and evacuates a stool sample 6 into collection bag 20. The user then pulls draw string 32 via handle 36 which closes the collection bag 20 by pulling the slider 28 which zips zipper 26 closed. As the collection bag 20 is being closed, the spring beam 24 at the front of collection bag 20 begins to deflect backwards in response to the zipper 26 closure which moves the closing collection bag 20 under center support 14.

In addition, the stool specimen collector apparatus device 10 may have a drape 36 which covers the front of the collection bag 20. The drape 36 has an opening 38 in the top of the drape 36 to allow stool to pass into collection bag 20. After a stool has been evacuated into the collection bag 20, and as the collection bag 20 is being closed, the drape 36 falls in to cover the collection bag 20 to protect the collection bag 20 during the rest of the toileting process. After toileting, the drape 36 can be detached and disposed.

A shipping container (not shown) may be used to ship the stool specimen collector apparatus, both prior to use, and after use toward a laboratory for analysis. The shipping container may contain one or more over-bags (not shown) to contain the used stool specimen collector apparatus 10 prior to placing the stool specimen collector apparatus 10 into the shipping container. Alternatively, the side supports 16 and 18 may fold over the housing 12 in order to form a shipping container.

It is envisioned that components of the stool specimen collector apparatus are reusable. In one embodiment the support bracket 12, slider 28 and draw string 32 are reusable.

Other aspects and advantages of the invention are apparent upon consideration of the disclosure herein.

What is claimed is:

1. An apparatus for collecting a stool specimen, the apparatus comprising:

a retractable collection bag comprising a spring beam attached to a housing shaped to conform to a toilet seat comprising a center support and a portion for storage of said bag;

a slider movably attached to said housing and capable of engagement with said collection bag; and a draw string attached to said slider wherein activating said draw string causes said bag to be retracted into said portion.

2. The apparatus of claim 1 wherein said housing has instruction printed thereon or enclosed therewith.

3. The apparatus of claim 1 wherein said collection bag is opaque.

4. The apparatus of claim 1 wherein said collection bag is closeable.

5. The apparatus of claim 1 wherein said collection bag is removable from said housing.

6. The apparatus of claim 1 wherein said slider is slideable along an opening of said collection bag.

7. The apparatus of claim 1 wherein said draw string comprises a handle.

8. The apparatus of claim 1 wherein said housing, said slider and said draw string are reusable.

* * * * *

UNITED STATES PATENT AND TRADEMARK OFFICE
CERTIFICATE OF CORRECTION

PATENT NO.      : 6,415,455 B1
DATED           : July 9, 2002
INVENTOR(S)     : Sloan et al.

It is certified that error appears in the above-identified patent and that said Letters Patent is hereby corrected as shown below:

<u>Title page,</u>
Item [12], below United States Patent, and also at,
Item [75], Inventors: please replace "Slaon, III et al." with -- Sloan, III et al. --.

Signed and Sealed this

Nineteenth Day of November, 2002

Attest:

JAMES E. ROGAN
Attesting Officer        Director of the United States Patent and Trademark Office